United States Patent [19]

Mueller et al.

[11] 4,136,250
[45] Jan. 23, 1979

[54] POLYSILOXANE HYDROGELS

[75] Inventors: Karl F. Mueller; Eduard K. Kleiner, both of New York, N.Y.

[73] Assignee: Ciba-Geigy Corporation, Ardlsey, N.Y.

[21] Appl. No.: 817,405

[22] Filed: Jul. 20, 1977

[51] Int. Cl.$^2$ ............................................. C08G 77/04
[52] U.S. Cl. ................................ 528/29; 71/DIG. 1; 252/522; 260/827; 528/10; 528/25; 424/184; 351/160 R
[58] Field of Search .................... 71/DIG. 1; 424/184; 252/522; 351/160; 260/46.5 UA, 46.5 Y, 827, 46.5 E

[56] References Cited

U.S. PATENT DOCUMENTS

| | | | |
|---|---|---|---|
| 2,976,576 | 3/1961 | Wichterle et al. | 18/58 |
| 3,220,960 | 11/1965 | Wichterle et al. | 260/2.5 |
| 3,488,111 | 1/1970 | Isen | 351/160 |
| 3,488,215 | 1/1970 | Shepherd et al. | 117/124 |
| 3,509,234 | 4/1970 | Burlant et al. | 260/859 |
| 3,512,183 | 5/1970 | Sharp et al. | 3/1 |
| 3,520,949 | 7/1970 | Shepherd et al. | 260/857 |
| 3,551,556 | 12/1970 | Kliment et al. | 424/21 |
| 3,567,118 | 3/1971 | Shepherd et al. | 239/6 |
| 3,574,826 | 4/1971 | Shepherd et al. | 424/81 |
| 3,576,760 | 4/1971 | Gould et al. | 252/403 |
| 3,577,512 | 5/1971 | Shepherd et al. | 424/21 |
| 3,577,516 | 5/1971 | Gould et al. | 424/46 |
| 3,641,237 | 2/1972 | Gould et al. | 424/16 |
| 3,660,545 | 5/1972 | Wichterle | 264/1 |
| 3,660,563 | 5/1972 | Gould et al. | 424/81 |
| 3,674,901 | 7/1972 | Shepherd et al. | 424/27 |
| 3,695,921 | 10/1972 | Shepherd et al. | 117/72 |
| 3,697,643 | 10/1972 | Shepherd et al. | 424/63 |
| 3,700,573 | 10/1972 | Laizjer et al. | 204/159.13 |
| 3,714,288 | 1/1973 | Nordstrom | 260/827 |
| 3,732,865 | 5/1973 | Higuchi et al. | 128/260 |
| 3,746,567 | 7/1973 | Nordstrom | 260/827 |
| 3,808,178 | 4/1974 | Gaylord | 260/86.1 E |
| 3,829,531 | 8/1974 | Graff | 260/859 |
| 3,959,102 | 5/1976 | Wajs et al. | 204/159.13 |

FOREIGN PATENT DOCUMENTS 2228180  1/1973  Fed. Rep. of Germany.
1378971  1/1975  United Kingdom.

OTHER PUBLICATIONS

Chemical Abstracts, vol. 77, 1972, No. 89625t.

*Primary Examiner*—Melvyn I. Marquis
*Attorney, Agent, or Firm*—Luther A. R. Hall

[57] ABSTRACT

A water-insoluble hydrophilic gel comprising (A) about 20 to about 90% by weight of a hydrophilic (a) polymer of identical or different water-soluble monoolefinic monomers, or (b) copolymer of said water-soluble monomers with 1 to 80% (of total monomers) of water-insoluble, identical or different monoolefinic monomers; which polymer or copolymer is cross-linked with (B) about 10 to about 80% by weight of a terminal polyolefinic siloxane macromer having a molecular weight from about 400 to about 8500.

22 Claims, No Drawings

POLYSILOXANE HYDROGELS

BACKGROUND OF THE INVENTION

This invention relates to crosslinked hydrophilic polymers which are suitable for use as a carrier for medicaments and other active ingredients; as hydrophilic membranes for separation processes; bandages for wound treatments; body implants; e.g., artificial veins and coatings on glass, metal, wood or ceramics, and in particular, for use in applications where strength of the polymer article and high permeability to water and oxygen are required simultaneously, as in contact lenses.

Hydrogels have been described since 1956 (U.S. Pat. No. 2,976,576) and subsequently a large number of patents have been issued describing the synthesis and use of hydrogels based primarily on 2-hydroxyethyl methacrylate and, to a lesser extent, on N-vinylpyrrolidone. Typically, these hydrogels are crosslinked, water-swellable polymers made by copolymerization of 2-hydroxyethyl methacrylate. They are used as polymeric, inert carriers for active substances, which are slowly and controllably released from these carriers; such active substances may be drugs (U.S. Pat. Nos. 3,574,826; 3,577,512; 3,551,556; 3,520,949; 3,576,760; 3,641,237; 3,660,563); agricultural chemicals (U.S. Pat. Nos. 3,576,760); or fragrances (3,567,118; 3, 697,643).

Their uses as antifogging coatings (U.S. Pat. No. 3,488,215), body implants and bandages have also been described in U.S. Pat. Nos. 3,577,516; 3,695,921; 3,512,183; 3,674,901. The widely used soft contact lens consists of this material (U.S. Pat. Nos. 3,488,111; 3,660,545;).

In the pharmaceutical field the main interest lies in the slow and controllable release of drugs from such hydrogels. Drug-containing hydrogel preparations have been described as being in the form of bandages; subcutaneous implants; buccal devices, intrauterine devices, and eye inserts. They are made by complicated fabrication procedures which usually involves casting the monomer solution into a suitable mold and polymerizing in the presence of a free radical generating initiator.

The use of drug loaded hydrogel granules as an oral dose form has also been suggested (U.S. Pat. No. 3,551,556). It is indeed one of the most useful applications of this concept in medicine since it allows the delivery into the bloodstream of an orally taken drug to spread out over several hours in a reproducible manner. This eliminates wasteful and potentially dangerous peak drug concentrations in the blood, while prolonging the time during which preferred and effective drug levels in the blood are maintained.

Sparingly crosslinked, water-insoluble, hydrophilic polymers are known which are made by the copolymerization of a major amount of a hydrophilic monoolefinic monomer and a minor amount, ranging from 0.01 to 15% of said monoolefin, of a low molecular weight crosslinking agent.

These hydrophilic monoolefinic monomers are generally the monoesters of acrylic or methacrylic acid with polyfunctional alcohols. 2-Hydroxyethyl methacrylate is particularly widely used. The crosslinking agents are generally the diesters of the same acids with the same polyfunctional alcohols, and ethylene bis-methacrylate is particularly widely used.

The copolymerization is carried out in the presence of water (U.S. Pat. No. 3,220,960) or in a water-free system (U.S. Pat. No. 3,520,949). Low molecular weight as well as macromolecular, water-soluble substances, such as poly(ethylene oxide) monomethacrylate together with a minor amount of the corresponding bis-methacrylate have been used (U.S. Pat. No. 3,220,960) as monomers and crosslinking agents. The water-soluble, but hydrophilic copolymers and the process for their production have been modified in several directions and adapted to specific purposes, e.g., the production of soft contact lenses (U.S. Pat. No. 3,220,960 and Reissue No. 27,401), and the copolymerization in the presence of a linear polyamide resin in order to improve or modify the mechanical properties of shaped bodies formed from the polymers obtained (U.S. Pat. No. 3,520,949). However, in all modifications low molecular weight polyolefinic crosslinking agents, especially ethylene bis-methacrylate, were used in very small to moderate amounts never exceeding 20% of the amount of the monoolefinic monomer. Though the copolymers of the type described above could be modified to comply with the requirements of several different methods of using them, the mechanical properties in either the unswollen, i.e., water-free, or the swollen, i.e., equilibrium state with water, could not be satisfactorily adapted to meet all enduse requirements. It is known that hydrophilic polymers whose major constituents are monoesters of acrylic acid and methacrylic acid and a bifunctional alcohol (glycol) have glass transition temperatures or softening points between 55° C. and 80° C. For this reason said prior art articles are brittle and glassy in the dry state at temperatures below 55° C. After equilibration in water these prior art articles become soft and somewhat pliable, but also weak with respect to their flexural properties. In addition, said prior art articles are very susceptible to tearing shear forces if they are inadvertently damaged in any way. Specifically they are extremely friable in the swollen state.

In order to avoid the undesirable weak characteristics of articles produced by said prior art polymers, a medium made of a stronger polymeric material is used as a physical support, or the pre-polymerized mixture is filled with an insoluble material such as silica gel. These techniques, although they afford a certain amount of cohesive strength (the hydrogel material acting as a glue), produce articles which are still susceptible to glassy fracture in the dry state, and shear fracture in the swollen state within the interstitial regions of the article. By the same token, addition of fillers to the prepolymer modify the diffusion properties and water permeability of the article often in unacceptable manner. Of course, an opaque polymer cannot be used as a contact lens material.

Copending application Ser. No. 581,065, filed May 27, 1975 and now abandoned, describes a new class of hydrogel materials, which do not show these drawbacks, but are tough and flexible in the dry as well as in the swollen state. This is achieved by incorporation of a major amount of a hydrophobic high-molecular weight crosslinking agent, which gives macromeric, flexible crosslinks rather than the conventional short crosslinks, which lead to brittleness. Still, for many applications the oxygen permeability was too low, especially for compositions of low equilibrium water content. The combination of a low, but appreciable water content and high oxygen permeability is especially important in the soft-contact lens field; contact lenses should be high enough in water content to make wearing them comfortable, but not too high as to lead to optical distortions. On the other hand, they should show high oxygen permeability at these low degrees of swelling. At the same time they should be tough and flexible and yet suitable for machining and polishing.

It has long been known that silicone based polymers have high oxygen permeability and silicone based contact lenses have been described in British Pat. No. 1,170,810 and French Pat. No. 1,526,934 as well as German Offen. No. 2,228,180. In all these cases a silicone polymer forms the core of a contact lens, whose surface has to be specially treated in order to render it hydrophilic and compatible with the cornea of the eye. This is achieved by grafting a hydrophilic monomer onto the contact lens using free radicals generating radiation in the presence or absence of oxygen. This can be done either during or after fabrication of the contact lens, but in either case it is a complicated process and difficult to control. Diffusion of the monomer into the core has to be prevented because it leads to cloudiness and each lens has to be molded separately and because the soft and friable polysiloxane core cannot be machined. The ability to machine and polish a contact lens out of a small blank is a great advantage because it allows one to adjust the lens to individual needs with great precision.

It has now been discovered, that an unexpectedly ideal combination of useful properties can be obtained by synthesizing a hydrogel containing a major proportion of a polymeric polysiloxane based crosslinking agent. This combination of properties includes: hydrophilicity; oxygen permeability; flexibility and toughness in the dry and swollen state; biocompatibility; polishability and machinability in general; clarity; ease and economy of synthesis.

SUMMARY AND OBJECTS OF THE INVENTION

It is an object of the present invention to provide cross-linked hydrophilic copolymers with improved oxygen permeability and tissue compatibility having high flexibility and high elasticity both in substantially water-free state and in the swollen state, i.e., in equilibrium with water or aqueous fluids, such as animal body fluids, which are suitable for use as hydrophilic membranes for gas and fluid separation processes, bandages for wound treatment; body implants, e.g., artificial veins, contact lenses; coatings on glass, metal, wood or ceramics, and as a carrier for biologically active substances, e.g., drugs, herbicides, insecticides, fungicides, bactericides, and fragrances.

It is a further object of the present invention to provide cross-linked hydrophilic copolymers, suitable as described above, which possess high tensile strength in the swollen state.

It is a still further object of the invention to provide cross-linked hydrophilic copolymers, which possess the above-named improved properties and contain a variable, effective amount of biologically active materials, in particular, therapeutically active substances.

It has now been found that water-insoluble hydrophilic copolymers consisting essentially of a hydrophilic polymer of monoolefinic monomers crosslinked with a major amount of a di- or tri-olefinic polysiloxane based macromer and which may contain a biologically active substance, possess the above-named and further desirable properties. In the novel copolymers, the proportion of the terminal di- or tri-olefinic siloxane macromer is a major proportion of the system amounting to about 10 to about 80% of the hydrophilic polymer or preferably from about 15 to 60%. The said terminal di- or tri-olefinic siloxane macromer has a molecular weight between about 400 and about 8500 or preferably between about 600 and about 5000.

DETAILED DESCRIPTION

This invention pertains to a water-insoluble hydrophilic gel comprising the crosslinked copolymerization product of (A) about 20 to about 90% by weight of said gel of (a) a water-soluble monoolefinic monomer, or mixture of said monomers, or (b) a water-soluble monomer, or mixture of said monomers, with 1 to 80% by weight of total monomers of a water-insoluble monoolefinic monomer, or mixture of said water-insoluble monomers, with (B) about 10 to about 80% by weight of said gel of a terminal polyolefinic hydrophobic siloxane macromer having a molecular weight from about 400 to about 8500, said macromer having the formula

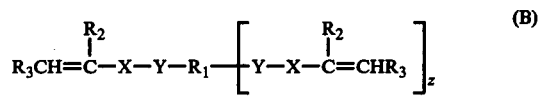

wherein $R_1$ is a polysiloxane chain having a molecular weight from about 200 to about 8000, and is of the formula

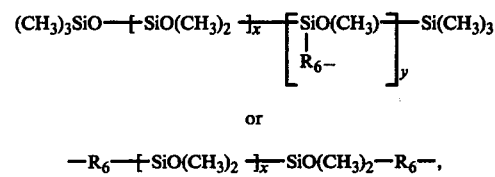

or $-R_6-\text{[}SiO(CH_3)_2\text{]}_{\overline{x}}-SiO(CH_3)_2-R_6-$, $R_2$ is hydrogen or methyl, $R_3$ is hydrogen or $-COOR_4$, $R_4$ is hydrogen or alkyl of 1 to 10 carbon atoms, and with the proviso that at least one of $R_2$ and $R_3$ is hydrogen, X is oxa, $-COO-$ or $-COR_5-$, $R_5$ is hydrogen or alkyl of 1 to 5 carbon atoms, $R_6$ is a branched or linear alkylene of 1 to 7 carbon atoms or $+CH_2CH_2O\frac{1}{n}$ where n is 1 to 20, x is an integer of 3 to 120, y is an integer of 2 to 3, z is an integer of 1 to 2, Y is the direct bond, the diradical $-R_7-Z_1-CONH-R_8-NHCO-Z_2-$, or $-R_7OCOCH_2CH_2S-$, $R_7$ is a linear or branched alkylene of 2 to 5 carbon atoms connected to X, $R_8$ is a diradical obtained by removing the NCO groups from an aliphatic, cycloaliphatic or aromatic diisocyanate, $Z_1$ is oxa or $-NR_5-$, $Z_2$ is $Z_1$ or thia and is connected to $R_6$, with the proviso that if X is oxa, Y is different from a direct bond and $R_2$ and $R_3$ are hydrogen.

The novel hydrogels of this invention are synthesized by free radical copolymerization, either in solution or in bulk, of a water-soluble monomer, (As) capable of forming a water-soluble or water-swellable polymer, i.e., hydrophilic polymer (Ap), with a di- or tri-olefinic siloxane derived macromer (B), for example, a compound consisting of a long, linear polysiloxane chain, terminated on both ends with a polymerizable vinyl group. In this way a three-dimensional macromolecular network is formed composed of two types of segments, each segment contributing its distinct physical properties to the system. The A-segment contributes water-solubility; the siloxane B-segment forms flexible crosslinks and improves oxygen permeability and tissue compatibility. By varying the relative proportions of each compound, a wide range of mechanical and diffusional properties may be obtained. For example, polymers having excellent strength and elongation as well as toughness, and yet being capable of absorbing as much as approximately their own weight of water, can be obtained by using the proper relative proportions of A and B. This is in contrast to conventional hydrogels, whose crosslinks are short and non-elastic and which, in the dry state, are hard and brittle.

The novelty of the polymers of the present invention resides in the incorporation of the di- or tri-functional macromolecule B as a major proportion of this system. In this manner, the di-functional macromer does not only serve as a structural crosslink, but also imparts its unique physical properties to the gel.

The hydrophilic polymer, Ap, is preferably a polymer of one or more water-soluble monoolefinic monomers, As, but it may also be a copolymer of monoolefinic water-soluble monomers, with at most 30%, preferably at most 40%, of the total amount of monomers, of a water-insoluble monoolefinic monomer, Ai.

The water-soluble monomers, As, are preferably acrylic and/or methacrylic acid or the water-soluble derivatives thereof, such as hydroxyalkyl esters where alkyl is 2 to 4 carbon atoms, e.g., 2-hydroxyethyl, 3-hydroxypropyl, 2-hydroxypropyl or 2,3-dihydroxypropyl esters; also ethoxylated and polyethoxylated hydroxyalkyl esters such as esters of alcohols of the formula

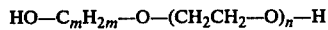

$$HO-C_mH_{2m}-O-(CH_2CH_2-O)_n-H$$

where
  m represents 2 to 5 and
  n represents 1 to 20 or esters of analogous alcohols, wherein a part of the ethylene oxide units is replaced by propylene oxide units. Also suitable are 3-(dimethylamino)-2-hydroxypropyl esters and amides. Another class of suitable derivatives of such acids are their water-soluble amides, such as unsubstituted amides and amides substituted by lower hydroxyalkyl, lower oxaalkyl or lower dialkylaminoalkyl groups where alkyl is 2 to 4 carbon atoms such as N-(hydroxymethyl)-acrylamide and -methacrylamide, N-(3-hydropropyl)acrylamide, N-(2-hydroxyethyl)methacrylamide and N-[1,1-dimethyl-2-(hydroxymethyl)-3-oxabutyl]acrylamide; water-soluble hydrazine derivatives, such as dimethyl-2-hydroxypropylamine methacrylimide and the corresponding derivatives of acrylic acid.

Also useful, in combination with comonomers, are the lower hydroxyalkyl maleic esters and vinyl ethers where alkyl is 2 to 4 carbon atoms, for instance, di-(hydroxyalkyl) maleates, such as di-(2-hydroxyethyl) maleate, and ethoxylated hydroxyalkyl maleates, hydroxyalkyl monomaleates, such as 2-hydroxyethyl monomaleate and alkoxylated hydroxyalkyl monomaleate with vinyl ethers, vinyl esters, styrene or generally any monomer which will easily copolymerize with maleates or fumarates; hydroxyalkyl vinyl ethers, such as 2-hydroxyethyl vinyl ether, 4-hydroxybutyl vinyl ether, with maleates, fumarates, or generally all monomers which will easily copolymerize with vinyl ethers.

Especially valuable as water-soluble monomers are hydroxyalkyl acrylates and methacrylates, such as 2-hydroxyethyl acrylate, 2-hydroxyethyl methacrylate, 2-hydroxypropyl acrylate, 3-hydroxypropyl methacrylate, 2,3-dihydroxypropyl methacrylate. Preferred hydroxy substituted vinyl monomers are 2-hydroxyethyl methacrylate and 2- and 3-hydroxypropyl methacrylate.

Most preferred is 2-hydroxyethyl methacrylate.

Water-soluble comonomers, which do not contain hydroxy groups are: acrylic and methacrylic acid and alkyl ethers of polyethoxylated hydroxyalkylesters thereof, such as esters of alcohols of the formula

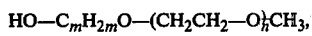

$$HO-C_mH_{2m}O-(CH_2CH_2-O)_nCH_3,$$

where
  m = 2 to 5 and
  n = 4 to 20 Dialkyl amino alkyl esters and amides, such as 2-(dimethylamino)ethyl,- or 2-(diethylamino)ethyl acrylate and methacrylate, as well as the corresponding amides; amides substituted by lower oxa-alkyl or lower dialkylamino alkyl groups, such as N-(1,1-dimethyl-3-oxa-butyl)acrylamide; water-soluble hydrazine derivatives, such as trialkylamine methacrylimide, e.g., triethylamine-methacrylimide and the corresponding derivatives of acrylic acid. Monoolefinic sulfonic acids and their salts, such as sodium ethylene sulfonate, sodium styrene sulfonate and 2-acrylamido-2-methylpropanesulfonic acid; or monoolefinic derivatives of heterocyclic nitrogen-containing monomers, such as N-vinylpyrrole, N-vinylsuccinimide, 1-vinyl-2-pyrrolidone, 1-vinylimidazole, 1-vinylindole, 2-vinylimidazole, 4(5)-vinylimidazole, 2-vinyl-1-methylimidazole, 5-vinylpyrazoline, 3-methyl-5-isopropenylpyrazole, 5-methylenehydantoin, 3-vinyl-2-oxazolidone, 3-methacrylyl-2-oxazolidone, 3-methacrylyl-5-methyl-2-oxazolidone, 3-vinyl-5-methyl-2-oxazolidone, 2- and 4-vinylpyridine, 5-vinyl-2-methylpyridine, 2-vinylpyridine-1-oxide, 3-isopropenylpyridine, 2- and 4-vinylpiperidine, 2- and 4-vinylquinoline, 2,4-dimethyl-6-vinyl-s-triazine and 4-acrylylmorpholine.

Preferred among these monomers are N-vinyl-2-pyrrolidone, 2-vinylpyridine, 4-vinylpyridine, 2-(dimethylamino) ethyl methacrylate, methacrylamide, acrylic acid and methacrylic acid.

Most preferred is N-vinyl-2-pyrrolidone.

These monomers can be used alone or in combination with each other and other suitable vinyl monomers, which may also be hydrophobic. The amount of such hydrophobic monomers shall not exceed 72% of the total composition and is preferably below 40%.

Suitable hydrophobic comonomers, Ai, which may be incorporated in the hydrogel are for example, water-insoluble olefinic monomers, such as alkyl acrylates or methacrylates in which alkyl has 1 to 18 carbon atoms, e.g., methyl and ethyl methacrylate or acrylate; vinyl esters derived from alkanecarboxylic acids having 1 to 5 carbon atoms, e.g., vinyl acetate and vinyl propionate, or vinyl benzoate. Acrylonitrile; styrene; and vinyl alkyl ethers in which the alkyl portion of the ether chain has 1 to 5 carbon atoms, e.g., methyl, ethyl, propyl, butyl or amyl vinyl ether.

Preferred are alkyl acrylates and alkyl methacrylates where the alkyl group is of 1 to 5 carbon atoms; vinyl acetate; styrene; and acrylonitrile.

The hydrophilic portion of the hydrogel composition is prepared by the polymerization of a water-soluble monoolefinic monomer or a mixture of said monomeres and which can contain from 0 to 80%, by weight of the total amount of the monomers of a water-insoluble monomers.

In the terminal diolefinic macromer hydrophobic crosslinking agent (B) its olefinic moieties are preferably provided by acyl groups of lower $\alpha,\beta$-monounsaturated aliphatic monocarboxylic or dicarboxylic acids or by vinyloxy moieties. These vinyl moieties are linked by a connecting group, such as provided by a diisocyanate, to a macromolecular chain containing repeating siloxane groups. The molecular weight of the macromer may vary from about 400 to about 8500, preferably between about 600 and 8500 and, especially, between about 1500 and 3000. Thus, the macromer preferably corresponds to the formula

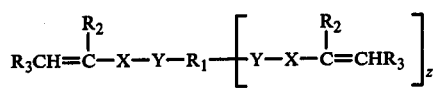
(B)

wherein $R_1$ is a polysiloxane chain having a molecular weight of about 400 to about 8000 and is of the formula

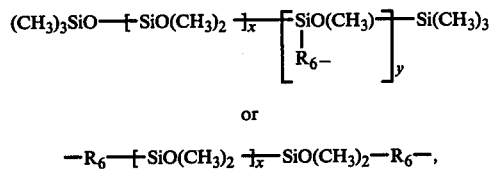

or $-R_6-[SiO(CH_3)_2\ ]_x-SiO(CH_3)_2-R_6-$, $R_2$ is hydrogen or methyl, $R_3$ is hydrogen or $-COOR_4$, $R_4$ is hydrogen or alkyl of 1 to 10 carbon atoms, and with the proviso that at least one of $R_2$ and $R_3$ is hydrogen, X is oxa, $-COO-$ or $-CONR_5-$, $R_5$ is hydrogen or alkyl of 1 to 5 carbon atoms, $R_6$ is a branched or linear alkylene of 1 to 7 carbon atoms or $-(CH_2CH_2O)_n-$ where n is 1 to 20, x is an integer of 3 to 120, y is an integer of 2 to 3, z is an integer of 1 to 2, Y is the direct bond, the diradical $-R_7-Z_1-CONH-R_8-NHCO-Z_2-$, or $-R_7OCOCH_2CH_2S-$, $R_7$ is a linear or branched alkylene of 2 to 5 carbon atoms connected to X, $R_8$ is a diradical obtained by removing the NCO groups from an aliphatic, cycloaliphatic or aromatic diisocyanate, $Z_1$ is oxa or $-NR_5-$, $Z_2$ is $Z_1$ or thia and is connected to $R_6$, with the proviso that if X is oxa, Y is different from a direct bond and $R_2$ and $R_3$ are hydrogen.

The terminal radicals of the compounds of formula B are according to the definitions of $R_2$ and $R_3$, if X represents $-COO-$ or $CONR_5-$, the acyl radicals of acrylic or methacrylic acid or the monoacyl radicals of maleic, fumaric or itaconic acid, or of monoalkyl esters of these acids with straight or branched chain alkanols of 1 to 10 carbon atoms, such as methanol, ethanol, butanol, isobutyl alcohol or decanol, of if X represents oxygen (oxa), the vinyloxy radical of vinyl ethers. Compounds of the formula B with Y being a direct bond are polyesters of macromolecular polyols, wherein hydroxy groups are attached to the polycondensate chain $R_1$, with $\alpha,\beta$-unsaturated acids. Such esters can be prepared from said macromolecular polyol by well-known acylation methods using reactive functional derivatives or suitable acids, e.g., chlorides of acrylic or methacrylic acid, or a monoalkyl esters of maleic, fumaric or itaconic acid, or the anhydride of maleic or itaconic acid.

According to the definition of formula B, Y can further be a divalent radical $-R_7-Z_1-CONY-R_8-NH-CO-Z_2-$. Therein $R_7$ is, e.g., methylene, propylene, trimethylene, tetramethylene, pentamethylene, neopentylene (2,2-dimethyltrimethylene), 2-hydroxytrimethylene, or 1-(dimethylaminomethyl) ethylene, and in particular ethylene. The divalent radical $R_8$ is derived from an organic diisocyanate and is an aliphatic radical such as alkylene, e.g., ethylene, tetramethylene, hexamethylene, 2,2,4-trimethylhexamethylene, 2,4,4-trimethylhexamethylene; fumaroyldiethylene or 1-carboxypentamethylene; a cycloaliphatic radical, e.g., 1,4-cyclohexylene or 2-methyl-1,4-cyclohexylene; and aromatic radical, such as m-phenylene, p-phenylene, 2-methyl-m-phenylene, 1,2-, 1,3-, 1,5-, 1,6- 1,7-, 1,8, 2,3- and 2,7-naphthylene, 4-chloro-1,2- and 4-chloro-1,8-naphthylene, 1-methyl-2,4-, 1-methyl-2,7, 4-methyl-1,2-, 6-methyl-1,3-, and 7-methyl-1,3-naphthylene, 1,8-dinitro-2,7-naphthylene, 4,4'-biphenylene, 3,3'-dichloro-4,4'-diphenylene, 3,3'-dimethoxy-4,4'-biphenylene, 2,2'-dichloro-5,5'-dimethoxy-4,4'-biphenylene, methylenedi-p-phenylene, methylenebis-(3-chlorophenylene), ethylenedi-p-phenylene or oxydi-p-phenylene. If in structure B, Y is not a direct bond, $R_6$ is always connected to X.

Y further can be the radical $-R_7OCOCH_2CH_2S-$ where $R_7$ is a linear or branched alkylene of 2 to 5 carbon atoms. Compounds with this connecting group are made by the base catalyzed addition of an alkylene bisacrylate to a polydimethyl siloxane dithiol in a molar ratio of 2 to 1.

Thus, compounds of the formula B, in which Y are said divalent radicals, are, if X represents oxygen, bisvinyl ethers or, if X represents $-COO-$ or

bis-acrylates, bis-methacrylates, bis-maleates, bis fumarates and bis-itaconates.

$R_1$ is in particular derived from macromeric polyols or dithiols of 200 to 8000 molecular weight (MW).

Compounds wherein Y is $-R_7-Z_1-CONH-R_8-NHCO-Z_2-$ are obtained in a two-step reaction by first reacting the polydimethyl siloxane diol, triol or dithiol with about two times the stoichiometric amount of an aliphatic, cycloaliphatic or aromatic diisocyanate consisting of two isocyanate (NCO) groups attached to the radical $R_8$ in order to endcap each $-OH$ or $-SH$ group in the siloxane molecule. In a second step, the isocyanate endcapped siloxane is reacted with a compound of the formula

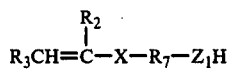  (C)

wherein $R_2$, $R_3$, X, $R_7$ and $Z_1$ are as defined above. Compounds of this type are described above as water soluble monomers having free hydroxyl groups.

If X represents oxygen, (C) is vinyl ether containing an active hydrogen, for instance an hydroxyalkyl vinyl ether or an aminoalkyl vinyl ether; if X represents —COO— or —CONR$_5$—, (C) is an acrylate, methacrylate, maleate, fumarate, itaconate or the corresponding amide, containing an active hydrogen in the substituted alkyl group. The macromolecular diol or diamine is preferably used in a small excess, i.e., the ratio of isocyanato groups to hydroxy or amino groups during the first step of the macromer synthesis should be at least 1:1, but is preferably at least 1:1.05. If the compound of formula C, used during the second step of the macromer synthesis, is the same as is used as the hydrophilic monomer, then a large excess of this compound can be used, so that the resulting solution of macromer B dissolved or dispersed in monomer A can be used directly for the preparation of the final hydrogel.

The more preferred siloxane macromers of formula B have a molecular weight in the range of about 600 to about 8500 and comprise a polysiloxane polyol or dithiol of molecular weight of about 400 to about 8000 first endcapped with isophorone diisocyanate or tolylene-2,4-diisocyanate and then reacted with a hydroxy compound selected from the group consisting of the hydroxyalkyl esters, where alkyl is 2 to 4 carbon atoms, of acrylic acid, methacrylic acid, maleic acid and fumaric acid, the hydroxy esters of said acids with an alcohol of the formula

where m is 2 to 5 and n is 1 to 20, and the hydroxyalkyl vinyl ethers where alkyl is 2 to 4 carbon atoms.

Preferably the hydroxy compound is 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, 2,3-dihydroxypropyl acrylate or 2,3-dihydroxypropyl methacrylate.

Most preferably the hydroxy compound is 2-hydroxyethyl acrylate or 2-hydroxyethyl methacrylate.

The polysiloxane polyol or dithiol is most preferably endcapped with isophorone diisocyanate and the hydroxy compound is most preferably 2-hydroxyethyl methacrylate.

The synthesis of the macromer, B, is suitably carried out at a temperature in the range of from about room temperature to approximately 80° C. Preferably, the temperature employed is not above 40° C., and most suitably is within the range of about 30°-40° C. The conversion of the isocyanato group is followed by infrared spectroscopy or by titration.

Preferred diisocyanates for preparing the macromer are tolylene-2,4-diisocyanate and isophorone diisocyanate.

Another method for preparing the macromer is by reacting a hydroxyl-terminated prepolymer, e.g., with acryloyl chloride, methacryloyl chloride or maleic anhydride and thus forming a macromer without connecting urethane linkages as, for example, a macromer where Y is a direct bond.

The free radical polymerization is started by an initiator capable of generating free peroxy or alkyl radicals in high enough concentration to initiate polymerization of the vinyl monomers employed at the synthesis temperature. These initiators are preferably peroxides or azo catalysts having a half-life at the polymerization temperature of at least 20 minutes. Typical useful peroxy compounds include: isopropyl percarbonate, tert.-butyl peroctoate, benzoyl peroxide, lauroyl peroxide, decanoyl peroxide, acetyl peroxide, succinic acid peroxide, methyl ethyl ketone peroxide, tert.-butyl peroxyacetate, propionyl peroxide, 2,4-dichlorobenzoyl peroxide, tert.-butyl peroxypivalate, pelargonyl peroxide, 2,5-dimethyl-2,5-bis(2-ethylhexanoyl-peroxy)hexane, p-chlorobenzoyl peroxide, tert.-butyl peroxybutyrate, tert.-butyl peroxymaleic acid, tert.-butyl-peroxyisopropyl carbonate, bis(1-hydroxycyclohexyl)peroxide; azo compounds include: 2,2-azo-bis-isobutyronitrile; 2,2'-azo-bis-(2,4-dimethylvaleronitrile); 1,1'-azo-bis-(cyclohexane carbonitrile), 2,2'-azo-bis-(2,4-dimethyl-4-methoxyvaleronitrile).

If the polymerization is carried out in water, water-soluble peroxy compounds can be used, such as sodium, potassium or ammonium persulfate, as well as free radicals generating redox systems, such as a persulfate-bisulfite combination. Other free radical generating mechanisms can be employed, such as X-rays, electron-beams and UV-radiation.

The amount of initiator can vary from 0.02% to 1% by weight of the monomer (A) and macromer (B), but is preferably from 0.03 to 0.3% by weight thereof.

The novel hydrophilic hydrogel copolymers of this invention are produced by free radical copolymerization, either in solution or in bulk, of water-soluble monoolefinic monomers, $A_s$, or a mixture of at least 20% of water-soluble monomers, $A_s$, with at most 80% of water-insoluble monoolefinic monomers, $A_i$, with from 10 to 80%, with reference to the total weight of the hydrogel, of macromers of the structure B. The polymerization is suitably carried out with a free radical generating initiator at a temperature in the range from about 40° C. to about 150° C., the preferred temperature ranges between about 50° C. and about 100° C. If a therapeutically or otherwise biologically active substance is present during the polymerization, its heat stability may be a limiting factor on the polymerization temperature.

One preferred method of preparing the hydrogel article comprises dissolving in the macromer-monomer solution, with a macromer-monomer ratio selected in such a way as to produce the desired mechanical and water absorption characteristics for the hydrogel, from about 0.02% to about 1%, by weight, of a suitable free radical initiator and polymerizing the mixture at, e.g., 80° C. for about 2 hours in a closed mold so as to produce a flat sheet of hydrogel containing the medicament as a quasi-solid solution. The sheet is then subjected to a high vacuum at about 100° C. for about 12 hours or extracted by swelling in solvents such as alcohols or water in order to remove residual monomers and initiator decomposition products.

A preferred laboratory method of preparation of the hydrogel, in the form of a cylinder, comprises the filling of flexible polyethylene tubing with the preferred composition of macromer, monomers, and catalyst and reacting the mixture for approximately 2 hours at 80° C. The finished article is removed by slitting the tubing longitudinally and stripping it away from the hydrogel article.

Yet another preferred method of preparation of the hydrogel, in the form of small spheres or beads, comprises polymerizing the preferred composition of macromer and monomers, and catalyst in a medium which is not a solvent for any part of the hydrogel composition at about 30° to 90° C. Examples of suitable bead polymerization media are silicone oils, polyfluorinated oils and the like, e.g., mineral spirits, and saturated aqueous salt solutions. In the latter case dispersing agents such as poly(vinyl pyrrolidone), hydroxyethylcellulose, magnesium hydroxide or calcium phosphates prevent coagulation.

Still another preferred method of preparation of the hydrogel in the form of a foamed object comprises the admixing of a common blowing agent, such as sodium bicarbonate, into the preferred composition and polymerizing the mixture in a mold at about 80° C. for about 1 hour. The resulting closed cell foam is particularly suitable for fast water absorption and medicament delivery.

The reaction if preferably carried out in an inert or anaerobic atmosphere if done in open molds. It is known that oxygen inhibits polymerization and gives rise to extended polymerization times for completion of the reaction. If closed molds are used to form the hydrogel article, the molds are composed of inert materials having low oxygen permeability and non-stick properties. Examples of suitable molding materials are Teflon ®, silicone rubber, polyethylene, and Mylar ®. Glass and metallic molds may be used if a suitable mold-releasing agent is employed.

Incorporation of a medicament into the hydrogel article may be accomplished either by dissolution or dispersion in the macromer solution, monomer solution or mixture thereof prior to addition of the free radical catalyst, or by diffusion of the medicament into the finished article after polymerization. If the medicament is inert to free radical attack, it is preferred to dissolve or disperse it in the macromer solution, monomer solution or mixture thereof prior to polymerization. If the medicament is susceptible to free radical attack, it is incorporated into the finished article, after polymerization, by diffusion from a solvent medium.

The hydrogel system, consisting essentially of the siloxane macromeric segment, B, and the hydrophilic segment $A_p$, may vary widely in composition and consequently the degrees of hydrophilicity and mechanical strength may be balanced to suit a wide variety of applications, such as for delivery systems for drugs, insecticides, herbicides, etc., as semi-permeable membranes in reverse osmosis, as body implants and bandages, or as material for contact lenses.

Hydrogels with leathery toughness in the dry state and high elongation in the wet state can be synthesized with water absorption ranging from low to high, dependent on the relative proportions of previously described components.

Hydrophilic membranes, which combine a relatively high weight wet strength with equilibrium water-contents of 5 to 50% are especially useful in applications, such as body-implants, bandages and semi-permeable membranes. For example, subcutaneous and intramuscular implants for the controlled release of medication must be capable of water absorption in a moderate range (15 to 25% by weight), yet be strong enough in the dry state and swollen state to withstand insertion and extraction procedures as well.

In addition to their suitability as medicament carriers, the hydrogels of the present invention are suitable for use as carriers for antiseptics, flavors, coloring agents, nutrients, insecticides, herbicides and the like. In particular, the hydrogels of the present invention may be swollen in an appropriate solvent containing the agent to be delivered; the solvent is evaporated, leaving the agent within the hydrogel particles. Upon contact with an aqueous environment, the agent will be released in a controlled manner.

Because of their good tissue compatibility and oxygen permeability in addition to a wide range of water absorptions and strength and elasticity, the hydrogels of the present invention are particularly suitable for use as intra-muscular and subcutaneous implants in warm-blooded animals and as contact lens material. For the same reasons, the hydrogel materials of the present invention may be fashioned into substituted blood vessels or extracorporeal shunts without the necessary supporting matrix used with otherwise relatively weak hydrogel materials.

The hydrogel materials of the present invention are also suitable for use as hydrophilic and non-thrombogenic coating since they adhere strongly to glass, metal and plastic. Because of their high strength and elasticity, they make strong coatings with high abrasion resistance useful for the coating of boat hulls to discourage barnacle growth, or the coating of lenses and glass to prevent fogging in high humidity enviroments.

Another unique attribute of the hydrogels of the present invention is their flexibility in the dry state such that they take on the shape desired in the application. A further advantage of the hydrogels of the present invention is realized in the swollen state inasmuch as they do not become friable, but retain strength and elasticity, even when fully equilibrated in an aqueous environment. These properties are particularly useful in membrane applications under pressure, such as in reverse osmosis apparatus, for which the hydrogels of the present invention are suitable. In addition to their toughness and flexibility, the polysiloxane hydrogels of this invention also show increased oxygen permeability which makes them superior candidates for contact lens materials.

Hydrogels of the present invention with medicaments contained therein are also particularly suitable for use in the treatment of open wounds and burns, due to their flexible form-fitting nature and simultaneous capability to carry medicaments directly to the affected area. A particular advantage of the hydrogels in this application is their flexibility in the dry state. It is not necessary to preswell the hydrogel before application in order to make it soft and pliable enough to wrap large injured areas and, thus the medicament-containing hydrogel may be stored dry, rather than in a swollen state, thereby increasing the shelf life of the medication contained therein.

Any of the drugs used to treat the body, both topical and systemic, can be incorporated as the active agent in the copolymeric carrier of this invention. "Drug" is used herein in its broadest sense as including any composition of matter that will produce a pharmacological or biological response.

Suitable drugs for use in therapy according to this invention include, without limitations, those listed in U.S. Pat. No. 3,732,865 (columns 10 and 11).

Other drugs having the same or different physiological activity as those recited above can be employed in carriers within the scope of the invention. Suitable mixtures of drugs can, of course, be dispensed with equal facility as with single component systems.

Drugs can be in various forms, such as uncharged molecules, components of molecular complexes, or nonirritating pharmacologically acceptable salts, e.g., the hydrochloride, hydrobromide, sulfate, phosphate, nitrate, borate, acetate, maleate, tartrate, salicylate, etc. For acidic drugs, salts of metals, amines, or organic cations (e.g., quaternary ammonium) can be employed. Furthermore, simple derivatives of the drugs (such as ethers, esters, amides, etc.) which have desirable retention and release characteristics, but which are easily hydrolyzed by body pH as well as enzymes, etc., can be employed.

The amount of drug incorporated in the carrier varies widely depending on the particular drug, the desired therapeutic effect, and the time span for which it takes the drug to be released. Since a variety of carriers in a variety of sizes and shapes are intended to provide complete dosage regimes for therapy for a variety of maladies, there is no critical upper limit on the amount of drug incorporated in the carrier. The lower limit, too, will depend on the activity of the drug and the span of its release from the carrier. Thus, it is not practical to define a range for the therapeutically effective amount of drug to be released by the carrier.

In addition to drugs, there can be incorporated in the copolymers of the instant invention fragrances or food flavors, such as orange oil, citral, coffee, tea, lemon oil, synthetic lemon-lime flavor, strawberry flavor, vanilla, biacetyl, anise, lilac fragrance, pie fragrance, peppermint oil, oil of orchids essence, anethole, ethyl propionate, ethyl acetate, acetaldehyde, menthol and spearmint, as well as pesticides including bactericides, fungicides, insecticides and nematocides.

Other examples for said biogicllly effective ingredients are listed in U.S. Pat. No. 3,660,563 (columns 3 to 7).

The novel hydrogels constitute a hybrid of three polymer types, combining the water swellability of conventional HEMA hydrogels, the strength of polyurethanes and the biological inertness of polysiloxanes in one polymer. Thus they are especially useful as biomedical plastics in contact with blood and tissue and may be considered excellent candidates for synthetic skin in the treatment of burns, as artificial organs with regard to the construction thereof or as a coating material thereon or as suture materials.

The hydrogel compositions may vary from 20 to 90% polymer ($A_p$) from monomer (A) and 10 to 80% siloxane macromer (B), corresponding to a typical degree of swelling of about 10 to 250%. The preferred compositions contain from about 15 to 60% macromer (B) and about 40 to 85% polymer ($A_p$), and range in their degree of swelling from 15 to 120%.

The following examples illustrate the invention. In these examples, the Degree of Swelling, DS, is defined as:

$$DS = \frac{\text{weight of swollen sample} - \text{weight of dry sample}}{\text{Weight of dry sample}} \times 100$$

The monomers and the diisocyanates useful in this invention are widely available as items of commerce.

The polydimethyl siloxane intermediates used to prepare the siloxane macromers are commercially available from the Dow Corning Chemical Company. Four such siloxane intermediates used in the instant examples have the following structures:

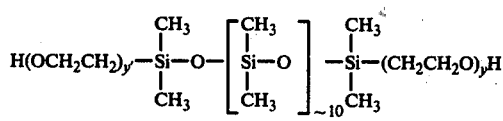

Q4-3667
$y + y' = 26$
(Molecular weight bout 2400)

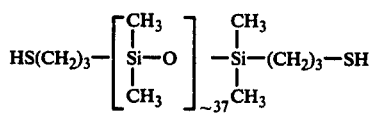

X2-8024
(Molecular weight about 3006)

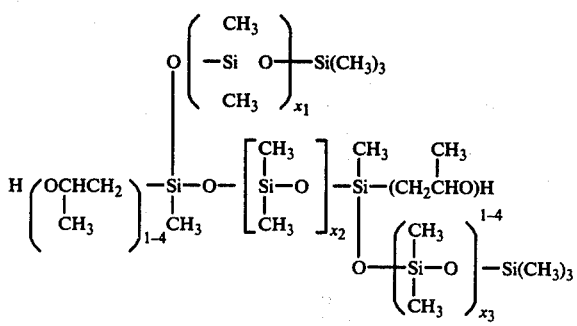

Q4-3557
$x_1 + x_2 + x_3 \sim 8$
(Molecular weight about 800)

-continued

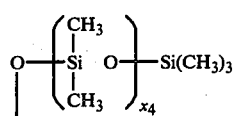

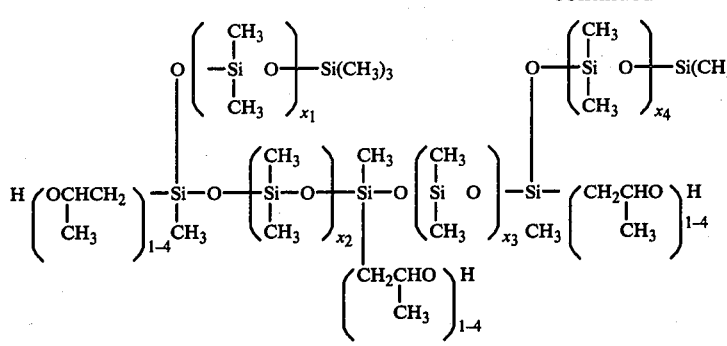

1248
$x_1 + x_2 + x_3 + x_4 \sim 70$
(Molecular weight about 6000)

The following examples are presented for the purpose of illustration only and are not to be construed to limit the nature or scope of the instant invention in any manner whatsoever.

EXAMPLE 1

Preparation of Siloxane Macromer

To a 1000 ml, 3-necked flask fitted with a mechanical stirrer, thermometer, condenser and nitrogen inlet were charged 480 grams (0.2 moles) of the polydimethyl siloxane diol, Q4-3667 of Dow Corning, molecular weight 2400, and 88.8 grams (0.4 moles) of isophorone diisocyanate. After adding 0.2 grams of triethylamine catalyst, the mixture was stirred under nitrogen at 60° C. for five hours till the isocyanate (NCO) content reached 2.78% (by titration, 2.95% theoretical).

500 grams of this polydimethyl siloxane diisocyanate prepolymer was diluted with 125 grams of 2-hydroxyethyl methacrylate to give an 87.3% solution of the siloxane prepolymer endcapped with methacrylate moieties (= siloxane macromer) in 2-hydroxyethyl methacrylate. This solution was stirred at room temperature till the isocyanate (NCO) band disappeared from the infrared spectra taken of the solution.

EXAMPLE 2

To 100 grams of the siloxane macromer solution prepared in Example 1 was added 0.1 gram of tert-butyl peroctoate. The macromer solution in 2-hydroxyethyl methacrylate was degassed for 30 minutes and then cast between "Teflon" coated aluminum sheets fitted with a 1/16 inch (1.588 mm) diameter silicon cord spacer. The sheet mold was cured at 80° C. for three hours with a one hour post-cure period at 100° C. After cooling, a translucent, very flexible polymer sheet of 1.5 mm thickness was obtained.

EXAMPLE 3

Following the procedure of Example 2, a sheet was prepared by the curing of a 43.7% solution of siloxane macromer in 2-hydroxyethyl methacrylate made by adding 50 grams of the macromer solution of Example 1 to 50 grams of 2-hydroxyethyl methacrylate.

EXAMPLE 4

Following the procedure of Example 2, a sheet was prepared by curing a 54.6% solution of siloxane macromer in N-vinylpyrrolidone and 2-hydroxyethyl methacrylate made by mixing 62.5 grams of the macromer solution of Example 1, 12.5 grams of 2-hydroxyethyl methacrylate and 25 grams of N-vinylpyrrolidone.

EXAMPLE 5

Preparation of Siloxane Macromer

Following the procedure of Example 1, another siloxane macromer was prepared by first reacting 160 grams (0.2 moles) of the polydimethyl siloxane diol, Q4-3557 of Dow Corning, molecular weight 800, and 88.8 grams (0.4 moles) of isophorone diisocyanate. The mixture was stirred for five hours at 50° C. under nitrogen till the NCO content reached 6.45% (by titration, 6.74% theoretical).

200 grams of the siloxane diisocyanate prepolymer was diluted with 50 grams of 2-hydroxyethyl methacrylate and stirred at room temperature till the NCO band disappeared in the infrared spectrum.

EXAMPLE 6

Following the procedure of Example 2, a sheet was prepared by curing a 72.5% solution of the siloxane macromer in 2-hydroxyethyl methacrylate made by adding 75 grams of the siloxane macromer solution of Example 5 with 25 grams of 2-hydroxyethyl methacrylate.

EXAMPLE 7

Following the procedure of Example 2, a sheet was prepared by curing a 48.4% solution of the siloxane macromer in N-vinylpyrrolidone and 2-hydroxyethyl methacrylate by mixing 75 grams of the siloxane macromer of Example 5 and 50 grams of N-vinylpyrrolidone.

EXAMPLE 8

Preparation of Siloxane Macromer

Following the procedure of Example 1, another siloxane macromer was prepared by first reacting 180 grams (0.03 moles) of the polydimethyl siloxane triol, 1248 of Dow Corning, molecular weight 6000, and 20 grams (0.09 moles) of isophorone diisocyanate. The mixture was stirred for twelve hours under nitrogen at 80° C., after 0.06 grams of 1,4-diazabicyclo[2.2.2]octane, "Dabco", was added as catalyst, till the NCO content reached 1.89% (by titration, 1.89% theoretical).

170 grams of the siloxane triisocyanate prepolymer was diluted with 42.5 grams of 2-hydroxyethyl methacrylate and stirred at room temperature till the NCO band disappeard in the infrared spectrum.

EXAMPLE 9

Following the general procedure of Example 2, a sheet was prepared by curing a mixture of 45 grams of the siloxane macromer solution of Example 8, 15 grams of N-vinylpyrrolidone, 60 grams of vinyl acetate and 0.12 grams of azobisiobutyronitrile catalyst. This mixture was degassed for 15 minutes and then cast between "Teflon" coated aluminum sheets equipped with a 1/16 inch (1.5885 mm) diameter silicon cord spacer. The sheet mold was cured at 50° C. for sixteen hours with a one-hour post-cure period at 100° C. After cooling, a hard translucent sheet was obtained.

EXAMPLE 10

Preparation of Siloxane Macromer

Following the procedure of Example 1, another siloxane macromer was prepared by first reacting 150.3 grams (0.05 moles) of the polydimethyl siloxane dithiol, X2-8024 of Dow Corning, molecular weight 3006, and 22.2 grams (0.10 moles) of isophorone diisocyanate. After adding 0.06 grams of triethylamine catalyst, the mixture was stirred under nitrogen at 50° C. for seven hours till the NCO content reached 2.72% (by titration, 2.43% theoretical).

100 grams of the siloxane diisocyanate prepolymer was diluted with 25 grams of 2-hydroxyethyl methacrylate and stirred at room temperature till the NCO band disappeared in the infrared spectrum.

EXAMPLE 11

Following the procedure of Example 9, a sheet was prepared by curing a mixture of 45 grams of the siloxane macromer solution of Example 10, 15 grams of N-vinylpyrrolidone, 60 grams of vinyl acetate and 0.12 grams of bisisobutyronitrile catalyst.

The various sheets prepared in Examples 2–4, 6, 7, 9 and 11 were measured for tensile strength and elongation both in the dry and wet (= swollen) state in equilibrium with water as well as degree of swelling both in water and in ethanol.

The results of these measurements are given on Table I. The degree of swelling (DS) in water or alcohol is determined by swelling a given weight of polymer in water or alcohol till equilibrium is established, weighing the swollen polymer and reweighing the dried sample. Degree of swelling is defined as:

$$DS = \frac{\text{weight of swollen beads} - \text{weight of dry polymer}}{\text{weight of dry polymer}} \times 100$$

macromer solution of Example 1 and 37.5 grams of 2-hydroxyethyl methacrylate.

EXAMPLE 13

Following the procedure of Example 2 a sheet was prepared by curing a 54.6% solution of the siloxane macromer in 2-hydroxyethyl methacrylate and methyl methacrylate. The solution was prepared by mixing 62.5 grams of the siloxane macromer solution of Example 1, 12.5 grams of 2-hydroxyethyl methacrylate, and 25.0 grams of methyl methacrylate.

EXAMPLE 14

Following the procedure of Example 2 a sheet was prepared by curing a 54.6% solution of the siloxane macromer in 2-hydroxyethyl methacrylate, N-vinyl-2-pyrrolidone, and methyl methacrylate. The solution was prepared by mixing 62.5 grams of the siloxane macromer solution of Example 1 and 12.5 grams of N-vinyl-2-pyrrolidone and 25.0 grams of methyl methacrylate.

EXAMPLE 15

Following the procedure of Example 2 a sheet was prepared by curing a 54.6% solution of the siloxane macromer in 2-hydroxyethyl methacrylate, and methyl methacrylate. The solution was prepared by mixing 62.5 grams of the siloxane macromer solution of Example 1 and 37.5 grams of methyl methacrylate.

EXAMPLE 16

Following the procedure of Example 2 a sheet was prepared by curing a 60.4% solution of the siloxane macromer in 2-hydroxyethyl methacrylate. The solution was prepared by mixing 62.5 grams of the siloxane macromer solution of Example 5 and 37.5 grams of 2-hydroxyethyl methacrylate.

EXAMPLE 17

Following the procedure of Example 2 a sheet was prepared by curing a 60.4% solution of the siloxane macromer in 2-hydroxyethyl methacrylate and N-vinyl-2-pyrrolidone. The solution was prepared by mixing 62.5 grams of the siloxane macromer solution of Example 5 and 12.5 grams of 2-hydroxyethyl methacrylate and 25.0 grams of N-vinyl-2-pyrrolidone.

Table I

| | | Composition | | | | Degree of Swelling % | | Tensile Strength (psi) | | Elongation (%) | |
|---|---|---|---|---|---|---|---|---|---|---|---|
| Example Number | Poly-siloxane | Meth-acrylate (1) % | (2) HEMAC % | (3) NVP % | (4) VAc % | DS $H_2O$ | DS EtOH | Dry | Wet | Dry | Wet |
| 2 | Q4-3667 | 87.3 | 12.7 | — | — | 31.5 | 106 | 183 | 112 | 83 | 32 |
| 3 | Q4-3667 | 43.7 | 56.3 | — | — | 40.0 | 132 | 1940 | 112 | 178 | 62 |
| 4 | Q4-3667 | 54.6 | 20.4 | 25 | — | 68.0 | 156 | 1992 | 69 | 43 | 19 |
| 6 | Q4-3557 | 72.5 | 27.5 | — | — | 7.0 | 43 | 4800 | 2230 | 24 | 49 |
| 7 | Q4-3557 | 48.4 | 1.6 | 50 | — | 58.0 | 127 | 4632 | 109 | 11 | 15 |
| 9 | 1248 | 31.8 | 5.2 | 12.5 | 50 | 25.0 | 203 | 2064 | 152 | 24 | 250 |
| 11 | X2-8024 | 32.3 | 5.2 | 12.5 | 50 | 21.0 | 176 | 3746 | 293 | 10 | 227 |

(1) Siloxane macromer endcapped with methacrylate moieties
(2) 2-hydroxyethyl methacrylate
(3) N-vinylpyrrolidone
(4) vinyl acetate

EXAMPLE 12

Following the procedure of Example 2 a sheet was prepared by curing a 54.6% solution of the siloxane macromer in 2-hydroxyethyl methacrylate. The solution was prepared by mixing 62.5 grams of the siloxane

EXAMPLE 18

Following the procedure of Example 2 a sheet was prepared by curing a 60.4% solution of the siloxane macromer in 2-hydroxyethyl methacrylate, N-vinyl-2-pyrrolidone, methyl methacrylate. The solution was prepared by mixing 62.5 grams of the siloxane macromer solution of Example 5 and 25.00 grams of N-vinyl-2-pyrrolidone and 12.5 grams of methyl methacrylate.

EXAMPLE 19

Following the procedure of Example 2 a sheet was prepared by curing an 84.6% solution of the siloxane macromer in 2-hydroxyethyl methacrylate and N-vinyl-2-pyrrolidone. The solution was prepared by mixing 87.5 grams of the siloxane macromer solution of Example 5 and 12.5 grams of N-vinyl-2-pyrrolidone.

The various sheets prepared in Examples 12–19 were measured for tensile strength and elongation both in the dry and wet (=swollen) state in equilibrium with water as well as the degree of swelling in both water and in ethanol. The results of these measurements are given on Table II.

Table II
PHYSICAL DATA

| Example Number | Composition Polysiloxane | Meth-acrylate (1) % | (2) HEMA % | (3) NVP % | (4) MMA % | Degree of Swelling % DS H$_2$O | DS EtOH | Tensile Strength Dry (psi) | Wet | Elongation Dry (%) | Wet |
|---|---|---|---|---|---|---|---|---|---|---|---|
| 12 | Q4-3667 | 54.6 | 45.4 | — | — | 33.5 | 92.5 | 2100 | 50 | 32 | 11 |
| 13 | Q4-3667 | 54.6 | 20.4 | — | 25 | 17.6 | 84.9 | 2240 | 500 | 198 | 119 |
| 14 | Q4-3667 | 54.6 | 7.9 | 12.5 | 25 | 32.7 | 111.2 | 2400 | 360 | 74 | 82 |
| 15 | Q4-3667 | 54.6 | 7.9 | — | 37.5 | 14.3 | 73.7 | 2030 | 890 | 145 | 108 |
| 16 | Q4-3557 | 60.4 | 39.6 | — | — | 10.1 | 58.8 | 5020 | 1370 | 8 | 37 |
| 17 | Q4-3557 | 60.4 | 14.6 | 25 | — | 17.3 | 61.3 | 5820 | 1000 | 6 | 26 |
| 18 | Q4-3557 | 60.4 | 2.1 | 25 | 12.5 | 16.1 | 63.1 | 6780 | 1750 | 11 | 21 |
| 19 | Q4-3557 | 84.6 | 2.9 | 12.5 | — | 6.3 | 45.5 | 4450 | 2290 | 11 | 16 |

(1) Siloxane macromer endcapped with methacrylate moieties
(2) 2-hydroxyethyl methacrylate
(3) N-vinyl-2-pyrrolidone
(4) methyl methacrylate The following Examples 20–22 describe the synthesis and evaluation of films for gas diffusion measurements.

EXAMPLE 20

To 10 grams of the siloxane macromer solution prepared in Example 4 was added 0.01 grams tert.-butyl peroctoate. The macromer solution was degassed for thirty minutes and then cast between Mylar lined glass plates with a 5 mil (0.127 mm) thick Mylar spacer. The sheet mold was cured at 80° C. for three hours with a one hour post cure period at 100° C. After cooling a clear flexible polymer sheet of about 3.5 mils (0.089 mm) thickness was obtained.

EXAMPLE 21

Films were prepared following the procedure in Example 20 with the compositions of Examples 12, 13, 16 and 18. Oxygen diffusion and permeability were measured in the dry state.

Table III

| Composition | $P_{30}^{1)} \times 10^{10}$ $\left(\dfrac{cm^3 \text{ (STP)} \times cm}{cm^2 \times sec \times cm\ Hg}\right)$ | $D_{30}^{2)} \times 10^7$ (cm$^2$/sec) |
|---|---|---|
| Example 4 | 23.76 | 9.47 |
| 12 | 33.99 | 16.09 |
| 13 | 4.84 | 2.87 |
| 16 | 9.67 | 5.24 |
| 18 | 5.61 | 1.99 |
| High density polyethylene[3)] | 0.4 | |
| Natural Rubber[3)] | 23.3 | |
| Poly(ethyl methacrylate)[3)] | 0.0103 | 1.15 |
| Polymer prepared from 2-hydroxyethyl methacrylate (70%) and poly-tetramethylene oxide (MW 2000 end-capped by 2-(isophorone isocyanato) ethyl methacrylate (30%) | 0.434 | 0.384 |

[1)]Permeability coefficient at 30° C
[2)]Diffusion coefficient at 30° C
[3)]Polymer Handbook, 2nd Edition pp. 234–235
Poly(2-hydroxyethyl methacrylate) (Hydron) could not be measured in the dry state because it is too brittle.

EXAMPLE 22

Oxygen permeability of swollen hydrogel films was determined using films equilibrated in water.

| | $DS_{H_2O}$ | $P_{25}^{1)} \times 10^{10}$ $\left(\dfrac{cm^3 \text{ (STP)} \times cm}{cm^2 \times sec \times cm\ Hg}\right)$ |
|---|---|---|
| Polymer Film of Example 12 | 33.5 | 13.6 |
| Poly(2-hydroxyethyl methacrylate) film (Hydron) | 64 | 7.5 |

Despite the lower water content of the polysiloxane hydrogel, its oxygen permeability is about double that of a conventional hydrogel.

[1)]Permeability coefficient at 25° C; Polymer Handbook, 2nd Edition pp. 234–235.

What is claimed is:
1. A water-insoluble hydrophilic gel comprising the crosslinked copolymerization product of
(A) about 20 to about 90% by weight of said gel of (a) a water-soluble monoolefinic monomer, or mixture of said monomers, or (b) a water-soluble monomer, or mixture of said monomers, with 1 to 80% by weight of total monomers of a water-insoluble monoolefinic monomer, or mixture of said water-insoluble monomers, with (B) about 10 to about 80% by weight of said gel of a terminal polyolefinic hydrophobic siloxane macromer having a molecular weight from about 400 to about 8500, said macromer having the formula $$R_3CH=C(R_2)-X-Y-R_1-[Y-X-C(R_2)=CHR_3]_z \quad (B)$$

wherein $R_1$ is a polysiloxane chain having a molecular weight from about 200 to about 8000, and is of the formula $$(CH_3)_3SiO-[SiO(CH_3)_2]_x-[SiO(CH_3)(R_6-)]_y-Si(CH_3)_3$$

or $$-R_6-[SiO(CH_3)_2]_x-SiO(CH_3)_2-R_6-,$$

$R_2$ is hydrogen or methyl,
$R_3$ is hydrogen or —COOR$_4$,
$R_4$ is hydrogen or alkyl of 1 to 10 carbon atoms, and with the proviso that at least one of $R_2$ and $R_3$ is hydrogen,
X is oxa, —COO— or —CONR$_5$—,
$R_5$ is hydrogen or alkyl of 1 to 5 carbon atoms,
$R_6$ is a branched or linear alkylene of 1 to 7 carbon atoms or —(CH$_2$CH$_2$O)$_n$— where n is 1 to 20,
x is an integer of 3 to 120,
y is an integer of 2 to 3,
z is an integer of 1 to 2,
Y is the direct bond, the diradical —R$_7$Z$_1$—CONH—R$_8$—NHCO—Z$_2$—, or —R$_7$OCOCH$_2$CH$_2$S—,
$R_7$ is a linear or branched alkylene of 2 to 5 carbon atoms connected to X,
$R_8$ is a diradical obtained by removing the NCO groups from an aliphatic, cycloaliphatic or aromatic diisocyanate,
$Z_1$ is oxa or —NR$_5$—,
$Z_2$ is $Z_1$ or thia and is connected to $R_6$, with the proviso that if X is oxa, Y is different from a direct bond and $R_2$ and $R_3$ are hydrogen.

2. A gel according to claim 1 wherein the water-soluble monomer is selected from the group consisting of acrylic acid, methacrylic acid and the water-soluble esters, amides and imides of said acids, salts of monoolefinic sulfonic acids and monoolefinic monocyclic azacyclic compounds.

3. A gel according to claim 1 wherein the water-soluble monomer is acrylic acid, methacrylic acid, a hydroxyalkyl or dialkylaminoalkyl ester of said acids in which alkyl is 2 to 4 carbon atoms.

4. A gel according to claim 1 wherein the water-soluble monomer is an acrylic acid or methacrylic acid ester of an alcohol of the formula $$HO-C_mH_{2m}-O-(CH_2CH_2O)_n-R$$

where R is hydrogen or methyl, m is 2 to 5 and n is 1 to 20.

5. A gel according to claim 1 wherein the water-soluble monomer is an amide or imide of acrylic or methacrylic acid in which the N-substituent is hydroxyalkyl, oxaalkyl or dialkylaminoalkyl where alkyl is 2 to 4 carbon atoms.

6. A gel as claimed in claim 1 wherein the water-soluble monomer is 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, 2,3-dihydroxypropyl acrylate, 2,3-dihydroxypropyl methacrylate or N-vinyl-2-pyrrolidone.

7. A gel according to claim 1 wherein the water-soluble monomer is 2-hydroxyethyl methacrylate.

8. A gel according to claim 1 wherein the water-soluble monomer is N-vinyl-2-pyrrolidone.

9. A gel according to claim 1 wherein the water-soluble monomer is a hydroxyalkyl maleate or fumarate where alkyl is 2 to 4 carbon atoms.

10. A gel according to claim 1 wherein the water-soluble monomer is a hydroxyalkyl vinyl ether where alkyl is 2 to 4 carbon atoms.

11. A gel according to claim 1 wherein the water-insoluble monomer is selected from the group consisting of the alkyl acrylates of methacrylates where alkyl is 1 to 18 carbon atoms, vinyl esters of alkanoic acids of 1 to 5 carbon atoms, vinyl benzoate, acrylonitrile, styrene and vinyl alkyl ethers where alkyl is 1 to 5 carbon atoms.

12. A gel according to claim 1 wherein the water-insoluble monomer is an alkyl acrylate or methacrylate where alkyl is 1 to 5 carbon atoms, vinyl acetate, styrene or acrylonitrile.

13. A gel according to claim 1 wherein the siloxane macromer with a molecular weight of about 600 to about 8500, and which comprises a polysiloxane polyol or dithiol of molecular weight of about 400 to about 8000 first endcapped with isophorone diisocyanate or tolylene-2,4-diisocyanate and then reacted with a hydroxy compound selected from the group consisting of the hydroxyalkyl esters, where alkyl is 2 to 4 carbon atoms, of acrylic acid, methacrylic acid, maleic acid and fumaric acid, the hydroxy esters of said acids with a alcohol of the formula $$HOC_mH_{2m}O(CH_2CH_2O)_nH$$

where m is 2 to 5 and n is 1 to 20, and the hydroxyalkyl vinyl ethers where alkyl is 2 to 4 carbon atoms.

14. A gel according to claim 13 wherein the hydroxy compound is 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, 2,3-dihydroxypropyl acrylate or 2,3-dihydroxypropyl methacrylate.

15. A gel according to claim 13 wherein the hydroxy compound is 2-hydroxyethyl acrylate or 2-hydroxyethyl methacrylate.

16. A gel according to claim 13 wherein the polysiloxane polyol or dithiol is endcapped with isophorone diisocyanate and the hydroxy compound is 2-hydroxyethyl methacrylate.

17. A gel according to claim 1 wherein about 15 to about 60% by weight of said gel is the siloxane macromer.

18. A pharmaceutical composition, comprising a gel as claimed in claim 1, together with a pharmacologically effective compound.

19. A fragrance composition, comprising a gel as claimed in claim 1, together with an odorant.

20. A pesticidal composition, comprising a gel as claimed in claim 1, together with a pesticide.

21. A herbicidal composition, comprising a gel as claimed in claim 1, together with a herbicide.

22. A gel according to claim 1 which is formed into a contact lens.

* * * * *

UNITED STATES PATENT AND TRADEMARK OFFICE
CERTIFICATE OF CORRECTION

PATENT NO. : 4,136,250

DATED : January 23, 1979

INVENTOR(S) : Karl Friedrich Mueller et al.

It is certified that error appears in the above—identified patent and that said Letters Patent is hereby corrected as shown below:

Column 4, line 35;
column 7, line 40; and
claim 1, column 21, line 22, on each line cancel:

$$\text{"}-R_6\left[SiO(CH_3)_2\right]_x SiO(CH_3)_2-R_6-\text{"}$$

and insert therefor :

$$\text{"}-R_6\left[SiO(CH_3)_2\right]_x Si(CH_3)_2-R_6-\text{"}$$

Signed and Sealed this

Twenty-ninth Day of September 1981

[SEAL]

Attest:

Attesting Officer

GERALD J. MOSSINGHOFF

Commissioner of Patents and Trademarks